(12) United States Patent
Chiba et al.

(10) Patent No.: US 8,137,703 B2
(45) Date of Patent: Mar. 20, 2012

(54) OZONE WATER AND PRODUCTION METHOD THEREFOR

(75) Inventors: Kaneo Chiba, Miyagi (JP); Masayoshi Takahashi, Ibaraki (JP)

(73) Assignees: REO Laboratory Co., Ltd., Monou-Gun, Miyagi (JP); National Institute of AIST, Tokyo (JP)

( * ) Notice: Subject to any disclaimer, the term of this patent is extended or adjusted under 35 U.S.C. 154(b) by 1403 days.

(21) Appl. No.: 10/591,978

(22) PCT Filed: Feb. 28, 2005

(86) PCT No.: PCT/JP2005/003811
§ 371 (c)(1),
(2), (4) Date: Sep. 5, 2006

(87) PCT Pub. No.: WO2005/085141
PCT Pub. Date: Sep. 15, 2005

(65) Prior Publication Data
US 2007/0205161 A1 Sep. 6, 2007

(30) Foreign Application Priority Data
Mar. 5, 2004 (JP) ................. 2004-062156

(51) Int. Cl.
*A01N 59/00* (2006.01)
*A01N 25/00* (2006.01)
*C02F 1/36* (2006.01)
*C02F 1/78* (2006.01)
*C02F 9/04* (2006.01)
*C02F 9/08* (2006.01)

(52) U.S. Cl. ............... 424/613; 210/150; 210/748.01; 210/748.19; 210/760; 261/83; 514/769

(58) Field of Classification Search ........................ None
See application file for complete search history.

(56) References Cited

U.S. PATENT DOCUMENTS

| 6,649,145 | B2 * | 11/2003 | McGrath et al. ................. 424/45 |
| 2003/0164306 | A1 | 9/2003 | Senkiw .......................... 205/633 |

FOREIGN PATENT DOCUMENTS

| JP | 122337/1985 | 8/1985 |
| JP | 10-251883 A | 9/1998 |
| JP | 2001-252664 A | 9/2001 |
| JP | 2002-307053 A | 10/2002 |
| JP | 2002-543960 A | 12/2002 |
| JP | 2003-334548 A | 11/2003 |
| JP | 2004-060010 | 2/2004 |
| WO | 03/022736 A1 | 3/2003 |

OTHER PUBLICATIONS

Bunkin et al., Colloids and Surfaces A: Physiochemical and Engineering Aspects (1996), vol. 110, pp. 207-212.*
Aquarius Technical Bulletin—No. 8 (2002), pp. 1-4.*
Didenko et al., Temperature of Multibubble Sonoluminescence in Water, J. Phys. Chem. A (1999), vol. 103, pp. 10783-10788.*
Goto, M., et al., "Nanobubble no Hassei Tokusei ni Kansuru Kenkyu", Dai 40 Kai Nippon Dennetsu Symposium Koen Ronbunshu, vol. II, pp. 359-360 (2003).
Kim, J.Y., et al., "Zeta Potential of Nanobubbles Generated by Ultrasonication in Aqueous Alkyl Polyglycoside Solutions", *Journal of Colloid and Interface Science*, 223 (2000).

* cited by examiner

*Primary Examiner* — Johann Richter
*Assistant Examiner* — Frank Choi
(74) *Attorney, Agent, or Firm* — Ladas & Parry, LLP

(57) ABSTRACT

The present invention relates to an ozone water that has the potential to find useful applications in a wide variety of technical fields and is capable of maintaining the effects of wiping out microorganisms such as bacteria, viruses and the like and inhibiting the growth thereof over long periods.

The present invention provides ozone nano-bubbles capable of staying in a solution for an extended period of time and a method for producing the ozone nano-bubbles by instantaneously shrinking the diameters of ozone microbubbles contained in an aqueous solution by the application of a physical irritation to the ozone microbubbles in an aqueous solution.

9 Claims, 4 Drawing Sheets

OZONE WATER AND PRODUCTION METHOD THEREFOR

TECHNICAL FIELD

The present invention relates to an ozone water that has the potential to find useful applications in every technical field and is capable of maintaining the effects of wiping out microorganisms such as bacteria, viruses and the like and inhibiting the growth of the microorganisms over a long period of time.

BACKGROUND ART

Ozone is known to have a strong oxidizing power and therefore has found extensive applications in various fields, e.g., sterilization, removal of odors, preservation of the freshness and the like. In particular, such a method is employed for disinfection of aqueous solutions, where an ozone-containing water prepared by placing ozone in gas bubbles contained in an aqueous solution is used.

For example, Japanese Patent Unexamined Publication (JP Kokai) 2004-60010 proposes an apparatus for efficiently dissolving ozone in an aqueous solution, that is, an apparatus for producing ozone-containing water where ozone is steadily dissolved in the aqueous solution.

The ozone-containing water as mentioned above shows high ozone contents when just produced. However, when the ozone-containing water is kept under normal temperature and pressure, ozone dissolved in the aqueous solution will mostly dissipate out in approximately one or two hours after the production of the ozone-containing water, for example, by diffusion from the surface of the aqueous solution. This means considerable decrease in the sterilizing effect. There has been the problem that long-term storage of the ozone-containing water is impossible.

DISCLOSURE OF THE INVENTION

In light of the above-mentioned circumstances, an object of the present invention is to provide an ozone water in which ozone is retained in an aqueous solution to exhibit an activating effect on biological materials, a sterilizing effect and the like over an extended period of time, and a method for producing the above-mentioned ozone water.

To discriminate between the conventional ozone-containing water and the one according to the present invention, the former will be referred to as ozone-containing water, and the latter, as ozone water.

An object of the present invention is to provide an ozone water where ozone is retained in an aqueous solution over long periods, and the above-mentioned object of the present invention can be achieved by an ozone water comprising an aqueous solution containing nano-bubbles in which ozone is held, the nano-bubbles having diameters of 200 nm or less.

Also, the above-mentioned object of the present invention can be effectively attained when the ozone concentration in the aqueous solution is 0.1 mg/L or more.

Another object of the present invention is to provide a method for producing an ozone water where ozone is retained in an aqueous solution over long periods. This object can be achieved by a method comprising the step of instantaneously shrinking ozone microbubbles in an aqueous solution to generate ozone nano-bubbles by the application of a physical irritation to the ozone microbubbles.

The above-mentioned object of the present invention can be advantageously achieved when the microbubbles are stopped from shrinking in such a manner that the charge density on the surface of each of the microbubbles is increased to evolve the electrostatic repulsive force when the bubble diameter is decreased to 200 nm or less in the step of instantaneously shrinking the microbubbles. Alternatively, the object of the present invention can be effectively achieved when the above-mentioned ozone nano-bubbles may be stabilized in such a manner that in the step of instantaneously shrinking the microbubbles, positively and negatively charged ions are electrostatically attracted to the ions adsorbed by the gas-liquid interface and drawn to a part adjacent to the above-mentioned interface in the aqueous solution, and therefore accumulated in high concentrations within a minute volume to form a shell surrounding each of the microbubbles, thereby inhibiting the ozone in the microbubbles from diffusing through the aqueous solution. Alternatively, the above-mentioned ozone nano-bubbles may be stabilized in such a manner that the above-mentioned ions adsorbed by the gas-liquid interface include hydrogen ion and hydroxide ion, and electrolytic ions in the aqueous solution are used as the ions to be drawn to the part adjacent to the interface. Alternatively, the object of the present invention can be advantageously achieved when the above-mentioned ozone nano-bubbles may be stabilized in such a manner that adiabatic compression that occurs in the step of instantaneously shrinking the microbubbles abruptly increases the temperature within each of the microbubbles, which leads to physicochemical changes involving an ultrahigh temperature around the microbubbles.

Furthermore, the above-mentioned object of the present invention can be effectively achieved when the physical irritation is caused by electrically discharging the microbubbles using a discharger; irradiating the microbubbles with ultrasonic waves using an ultrasonic generator; or creating a flow in the aqueous solution by actuating a rotor installed in a vessel where the aqueous solution is held, thereby taking advantage of compression, expansion and vortexes which occur when the flow is created. Alternatively, the object can be effectively achieved when the physical irritation is caused by compression, expansion and vortexes, in the case where a circulating circuit is provided in the above-mentioned vessel, in such a manner that the aqueous solution containing the microbubbles is introduced into the circulating circuit and then caused to pass through an orifice having a single opening or a plurality of openings or a porous plate which is provided in the circulating circuit.

Figure 1:
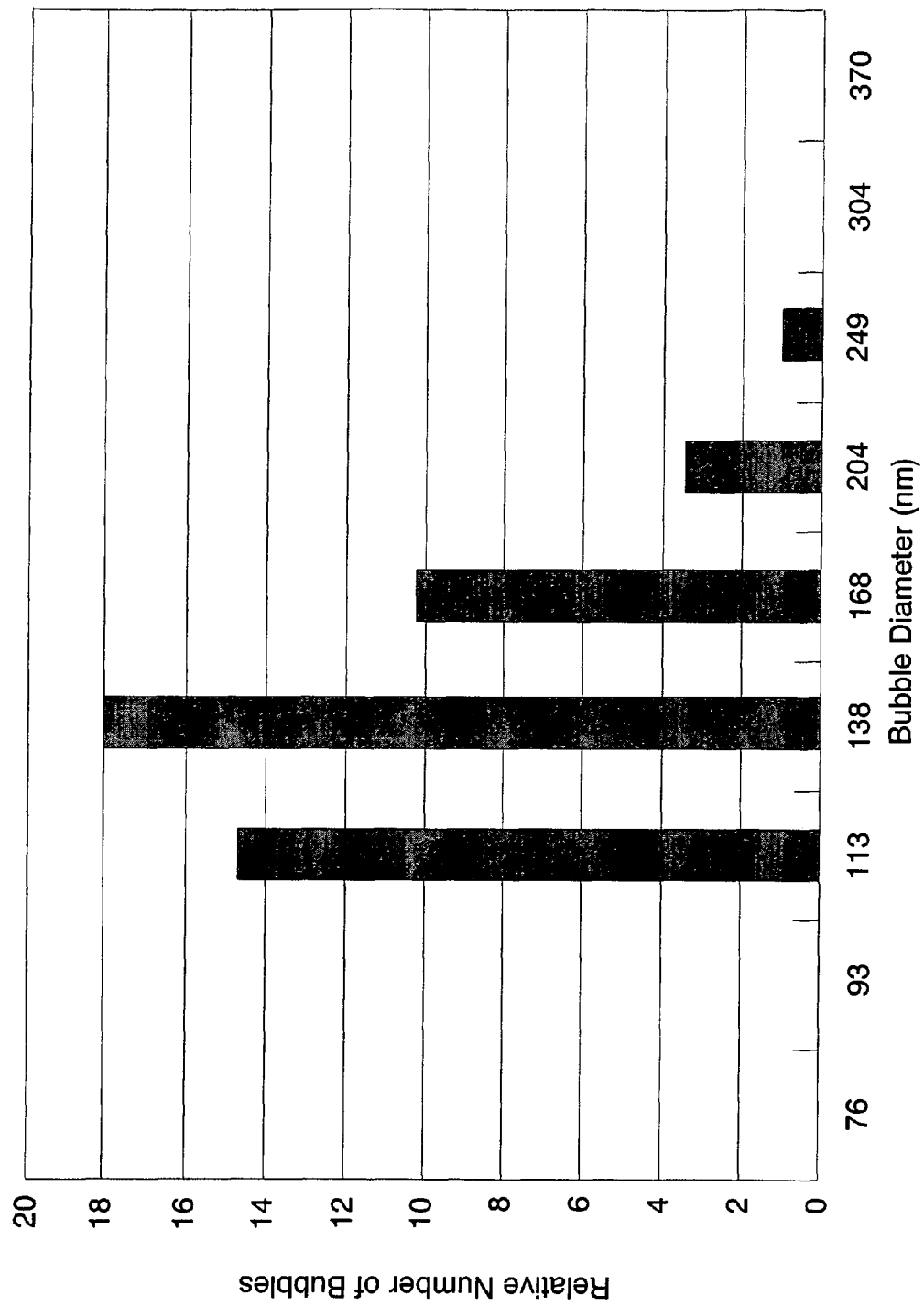
FIG. 1 is a graph showing the frequency distribution of particle diameter of ozone nano-bubbles contained in an ozone water of the present invention (wherein the mean distribution is about 140 nm and the standard deviation is about 30 nm).

REFERENCE NUMERALS 1 vessel
2 discharger
21 positive electrode
22 negative electrode
3 microbubble generator
31 intake
32 outlet for ozone nano-bubble containing aqueous solution
4 ultrasonic generator
5 circulating pump
6 orifice (porous plate)
7 rotor

BEST MODE FOR CARRYING OUT THE INVENTION

The ozone water of the present invention is characterized by comprising an aqueous solution containing ozone nano-bubbles which hold ozone therein, the bubbles having diameters of 200 nm or less. In the ozone water of the present invention, ozone can stay in the aqueous solution over an extended time period of one month or more to exhibit a variety of its effects. The ozone water according to the present invention will now be explained in detail.

In the ozone water of the present invention, ozone is retained in the form of nano-bubbles. The nano-bubble refers to a gas bubble with a diameter of 200 nm or less as shown in the particle size distribution in FIG. 1. The ozone nano-bubbles are characterized by being kept dissolved in the aqueous solution over an extended time period of one month or more. A preservation method for the ozone water according to the present invention is not particularly limited. Even though the ozone water is preserved in a container in common use, ozone will be retained in the aqueous solution without dissipation for one month or more.

Figure 2:
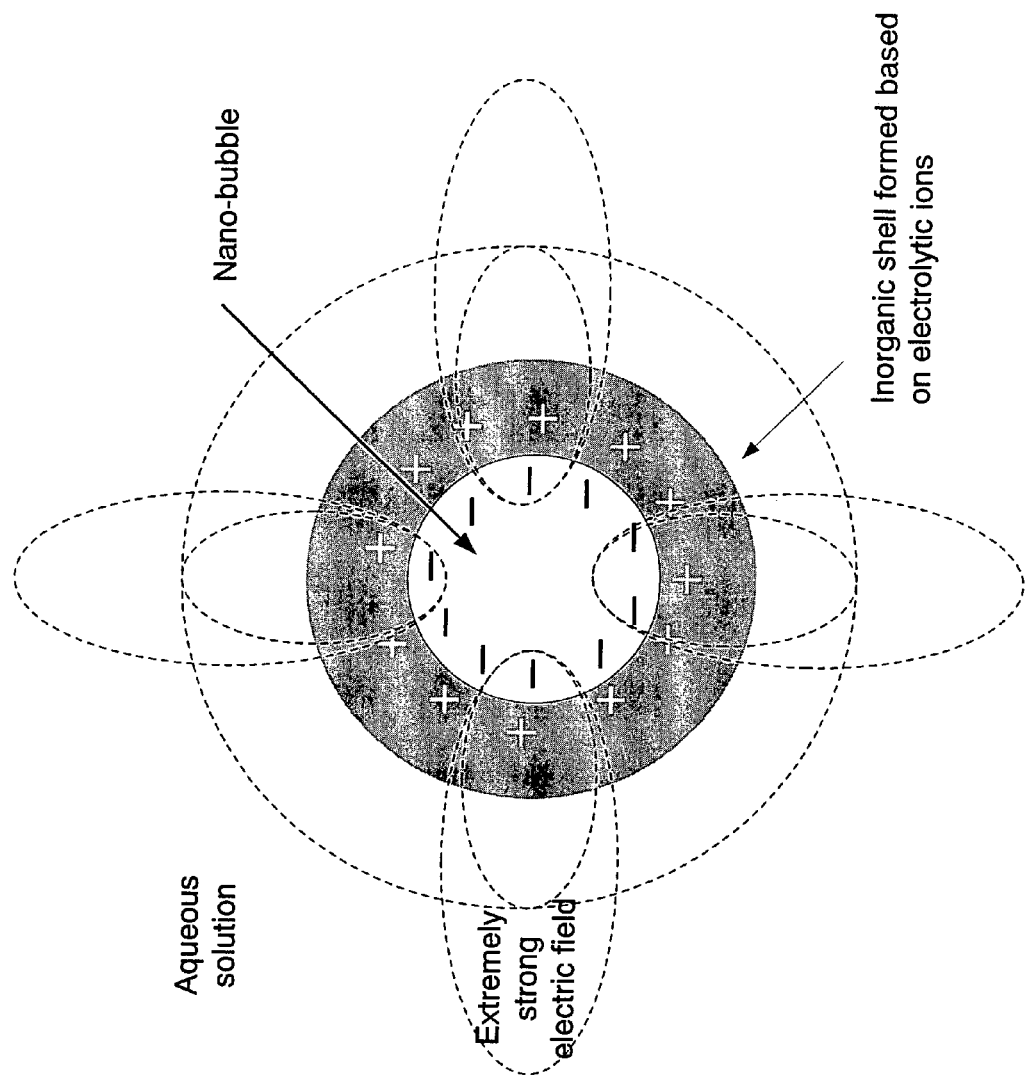
FIG. 2 is a schematic diagram illustrating the mechanism where ozone in the form of a nano-bubble is stable in an aqueous solution.

FIG. 2 shows the mechanism where ozone in the form of a nano-bubble is stabilized in an ozone water of the present invention. When ozone stays in the form of a microbubble, the smaller the size of bubble, the more the dissolution efficiency of the inner ozone is increased and the more unstable the bubble becomes, and then the bubble instantaneously disappears. In contrast to this, when ozone is in the form of a nano-bubble, electric charges are accumulated in extremely high concentrations on the gas-liquid interface and the electrostatic repulsive forces are generated between the charges present on the opposite sides of the bubble, thereby inhibiting the spherical bubble from shrinking. Also, by the action of a strong electric field formed by the concentrated ions, an inorganic shell consisting predominantly of electrolytic ions of iron or the like contained in the aqueous solution is formed around the bubble, which can prevent the inner ozone from dissipating. As distinct from shells made of surfactants and organic substances, the above-mentioned shell itself will readily collapse by dissipation of electric charges surrounding the nano-bubble when the ozone nano-bubble comes in contact with other substances such as bacteria and the like. When the shell is collapsed, ozone in the nano-bubble will easily be released into the aqueous solution.

As mentioned above, by the action of the concentrated electric field, an inorganic shell consisting predominantly of electrolytic ions of iron or the like is formed around the bubble, which can prevent the inner ozone from dissipating. The shell thus formed, which is different from shells made of surfactants and organic substances tends to readily collapse by itself because of dissipation of the electric charges surrounding the bubble when the ozone nano-bubble comes in contact with other substances such as bacteria and the like. The ozone is released and instantaneously decomposed to generate active oxygen and free radicals, which can be used to cause various chemical reactions, to wipe out microorganisms, to kill bacteria, and so on.

According to the method for producing the ozone water of the present invention, a physical irritation is applied to ozone-microbubbles with diameters of 10 to 50 µm to instantaneously shrink the bubbles. When electrolytes such as ions of iron, manganese, calcium, sodium, magnesium and other minerals are present in the aqueous solution containing ozone microbubbles so that the electric conductivity of the aqueous solution will reach 300 µS/cm or more, the electrostatic repulsive forces generated among those ions will inhibit the bubbles from shrinking. The above-mentioned electrostatic repulsive force refers to an electrostatic force acting on ions which are present on the opposite sides of the bubble and have the same polarity when the curvature of the bubble is increased in the process of shrinking the spherical microbubble. The ozone microbubble is pressurized in the shrinking process, so that the tendency of the microbubble to shrink becomes stronger as the shrinking of the microbubble proceeds. However, when the bubble diameter becomes smaller than 200 nm, the electrostatic repulsive force mentioned above appears and therefore the shrinking of the bubble is stopped.

When the electrolytes such as ions of iron, manganese, calcium, sodium, magnesium and ions of other minerals are mixed into the aqueous solution so that the electric conductivity of the aqueous solution will reach 300 µS/cm or more, the above-mentioned electrostatic repulsive force will act sufficiently, so that the tendency of the bubble to shrink and the repulsive force are balanced to stabilize the bubble. The diameter of the stabilized bubble (i.e., the diameter of the resultant nano-bubble), which varies depending upon the concentration and the kind of electrolytic ions is 200 nm or less as shown in FIG. 1.

In addition to the properties that ozone is retained in the nano-bubble under the application of pressure thereto, the ozone nano-bubble has the properties that an extremely strong electric field is formed by concentrated surface charges. The strong electric field mentioned above has the ability to significantly affect the ozone in the bubble and the aqueous solution around the bubble, which will lead to the effects of physiological activation and sterilization, and chemical reactivities and the like.

Figure 3:
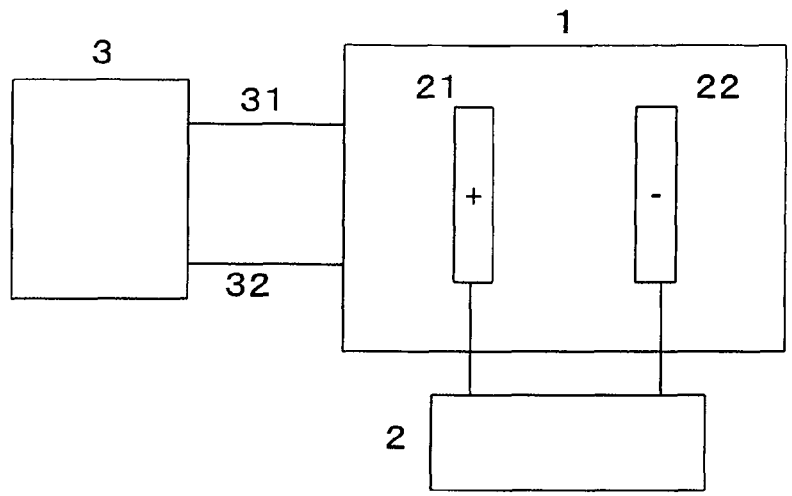
FIG. 3 is a side view showing an apparatus for producing an ozone water where a discharger is employed.

FIG. 3 is a side view showing an apparatus for producing an ozone water using a discharger.

An aqueous solution is brought into a microbubble generator 3 through an intake 31 from a vessel 1. The aqueous solution introduced through the intake 31 is mixed with ozone which is injected through an inlet (not shown) into the microbubble generator 3 to produce ozone microbubbles. Then, ozone microbubbles produced in the microbubble generator 3 are sent to the vessel 1 through an outlet for ozone nano-bubble containing aqueous solution 32. This cycle allows the ozone microbubbles to exist in the vessel 1. The vessel 1 is provided with a positive electrode 21 and a negative electrode 22, both of which are connected to a discharger 2.

First, ozone microbubbles are generated in the aqueous solution held in the vessel 1 using the microbubble generator 3.

Then, electrolytes such as iron, manganese, calcium and other minerals are added to the aqueous solution so that the electric conductivity of the aqueous solution will reach 300 µS/cm or more.

Using the discharger 2, electric discharge is carried out in the aqueous solution containing the ozone microbubbles in the vessel 1. In order to more efficiently produce ozone nano-bubbles, it is preferable that the concentration of the ozone microbubbles in the vessel 1 reach 50% or more of the saturated concentration. In addition, the electric discharge may preferably be carried out in water with the application of a voltage of 2,000 to 3,000 V.

By the application of impulse wave (physical irritation) induced by electric discharge in water, the ozone microbubbles in water are instantaneously shrunk to nano-level bubbles. At that time, the shrinking rate is too fast for the ions surrounding each bubble to flee into water, and consequently, the ions are instantaneously concentrated there in line with the progress of shrinking. The ions thus concentrated form an extremely strong electric field around the bubble. Under the application of such a strong electric field, hydrogen ion and hydroxide ion present on the gas-liquid interface establish a binding relationship with the electrolytic ions which are respectively charged oppositely to hydrogen ion and hydroxide ion and exist around the bubble, thereby forming an inorganic shell around the bubble. The shell can inhibit the ozone in the bubble from spontaneously dissolving into the aqueous solution, which can stabilize the ozone nano-bubbles in the aqueous solution without dissolution. The produced ozone nano-bubbles are extremely minute bubbles with diameters of about 200 nm or less, so that the bubbles are scarcely influenced by buoyancy in water. Therefore, the incidence of explosion on the water surface, which would be recognized for the ordinary bubbles is virtually zero with respect to the nano-bubbles.

The method for producing an ozone water by irradiating the microbubbles with ultrasonic waves as the physical irritation will now be explained. Explanations about the contents overlapping those mentioned above will be omitted.

Figure 4:
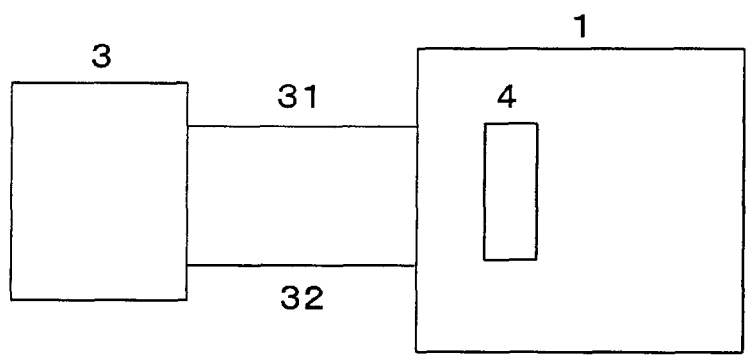
FIG. 4 is a side view showing an apparatus for producing an ozone water where an ultrasonic generator is employed.

FIG. 4 is a side view showing an apparatus for producing an ozone water using an ultrasonic generator.

Similar to the production method of ozone water by means of electric discharging, ozone microbubbles are generated using a microbubble generator 3, an intake 31 and an outlet for ozone nano-bubble containing aqueous solution 32, and the ozone microbubbles thus generated are sent to a vessel 1. An ultrasonic generator 4 is set in the vessel 1. The position of the ultrasonic generator 4 is not particularly limited, but preferably the ultrasonic generator 4 may be disposed between the intake 31 and the outlet for ozone nano-bubble containing aqueous solution 32 in order to efficiently generate the ozone nano-bubbles.

First, ozone microbubbles are generated in water containing electrolytic ions held in the vessel 1 using the microbubble generator 3.

Using the ultrasonic generator 4, ultrasonic wave is then applied to the aqueous solution containing the ozone microbubbles in the vessel 1. In order to efficiently produce ozone water, it is preferable that the concentration of the ozone microbubbles in the vessel 1 reach 50% or more of the saturated concentration. Preferably, the ultrasonic wave used may have frequencies of 20 kHz to 1 MHz. With respect to the ultrasonic irradiation, it is preferable that oscillation and suspension be repeated alternately at intervals of 30 seconds. Alternatively, continuous irradiation may be possible.

The production method of ozone water by creating a vortex flow as the physical irritation will now be explained. The contents overlapping those mentioned above will not be explained.

Figure 5:
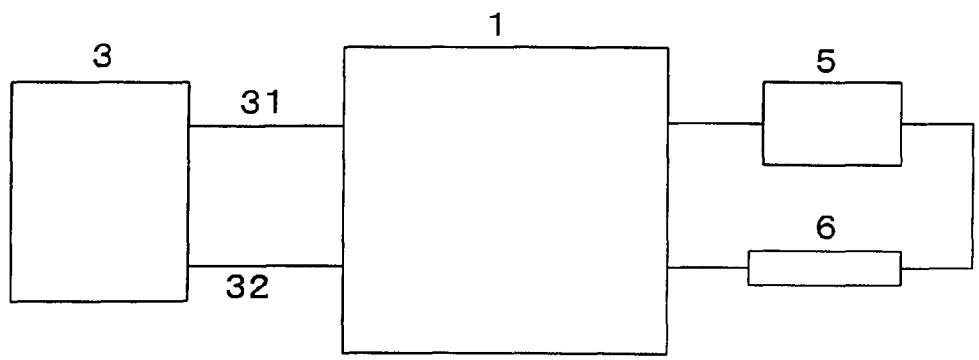
FIG. 5 is a side view showing an apparatus for producing an ozone water by generating a vortex flow.

FIG. 5 is a side view showing an apparatus for producing an ozone water by using compression, expansion, and vortex flow. Similar to the production methods of ozone water by means of electric discharging and ultrasonic irradiation, ozone microbubbles are generated using a microbubble generator 3, an intake 31 and an outlet for ozone nano-bubble containing aqueous solution 32, and the ozone microbubbles are sent to a vessel 1. A circulating pump 5 for partially circulating the aqueous solution containing ozone microbubbles in the vessel 1 is connected to the vessel 1. Within the piping (circulating piping) including the circulating pump 5, an orifice (porous plate) 6 having a plurality of openings is provided and connected to the vessel 1. The aqueous solution containing ozone microbubbles in the vessel 1 is caused to travel through the circulating piping by the action of the circulating pump 5 and pass through the orifice (porous plate) 6, whereby compression, expansion and vortexes are generated.

First, ozone microbubbles are generated in water containing electrolytic ions held in the vessel 1 using the microbubble generator 3.

Then, the circulating pump 5 is actuated to partially circulate the aqueous solution containing ozone microbubbles. By the action of the circulating pump 5, the aqueous solution containing ozone microbubbles is pushed out. Within the piping, compression, expansion and vortexes are generated before and after the solution is caused to pass through the orifice (porous plate) 6. The ozone microbubbles are electrically charged by the compression and expansion of the microbubbles when passing across the orifice and by the vortexes generated within the piping, to generate the eddy current. Thus, the ozone microbubbles are instantaneously shrunk and finally stabilized into ozone nano-bubbles. The order of the circulating pump 5 and the orifice (porous plate) 6 in the flow path may be reversed.

Figure 6:
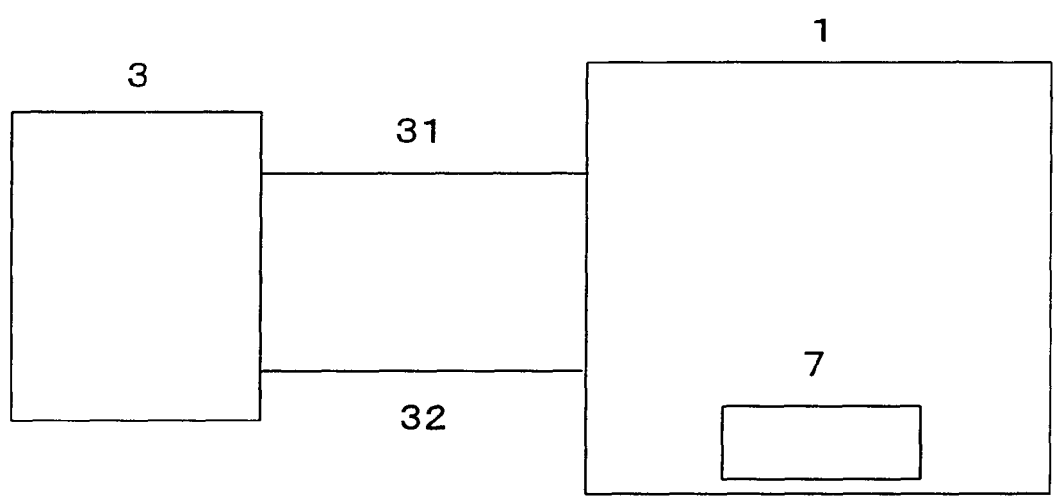
FIG. 6 is a side view showing an apparatus for producing an ozone water by actuating a rotor to generate a vortex flow.

A single orifice (porous plate) 6 is provided in FIG. 6, but a plurality of plates may be installed. The circulating pump 5 may be omitted as occasion arises. In such a case, the force of the microbubble generator 2 to drive the aqueous solution or a difference of altitude may be utilized for creating a flow in the aqueous solution.

As shown in FIG. 6, the ozone nano-bubbles can also be produced by installing a rotor 7 in a vessel 1 to generate a vortex flow therein. Preferably, the rotor 7 may be operated at 500 to 10,000 rpm to efficiently generate a vortex flow in the vessel 1.

The present invention will now be explained in detail with reference to the examples demonstrating the features and the effects of the ozone water according to the present invention, which examples are not intended to limit the present invention thereto.

Example

An ozone water according to the present invention having an ozone concentration of 1.5 mg/L immediately after the production was placed in a glass bottle, and stored in a cool, dark place with the bottle being covered with a lid.

One week after the production of ozone water, the ozone nano-bubbles in the ozone water of the present invention were observed using a dynamic light-scattering photometer. The nano-bubbles with a mean diameter of about 140 nm (with a standard deviation of about 30 nm) were found to be stable in water.

Six months later, the ozone concentration in the ozone water read 1.0 mg/L when measured by the ultraviolet absorption mode. It was confirmed that the amount of ozone contained in the ozone water was good enough for sterilization and the like.

The action of electrolytic ions plays an important role in stabilizing the ozone nano-bubbles in the ozone water of the present invention. The qualities of the ozone water according to the present invention were investigated. The results were as follows. pH: 8.06, electric conductivity: 22.3 mS/cm, iron: 0.01 mg/L, potassium: 130 mg/L, sodium: 3700 mg/L, magnesium: 350 mg/L.

In comparison with the above, the change in ozone concentration of an ozone-containing water prepared by bubbling of ozone was monitored. The ozone concentration was found to be 1.5 mg/L immediately after the production, but dropped to 0.1 mg/L or less two hours later. It was found that the degree of decrease in the ozone concentration of the above-mentioned ozone-containing water was not significantly changed even when other methods than the bubbling were employed to supply ozone into water.

Example 2

To investigate the sterilizing effect of the ozone water according to the present invention, 1000 mL of hot spring water taken from a hot spring source was mixed with the same amount of an ozone water of the present invention and the change in the number of bacteria was observed.

In the hot spring water the number of general bacteria was 96/1 ml; the number of colon bacilli was 20 MPN/100 ml; and the number of *Legionella* bacteria was 60 CFU/100 ml. The hot spring water was then mixed with 1000 mL of the ozone water of the present invention which had been produced one week before. As a result, the number of general bacteria was decreased to 0/1 ml; the number of colon bacilli, 0 MPN/100 ml; and the number of *Legionella* bacteria, less than 10 CFU/100 ml, which demonstrated a sufficient sterilizing effect.

EFFECTS OF THE INVENTION

According to the ozone water of the present invention and the production method therefor, ozone water contains ozone therein in the form of nano-bubbles with bubble diameters of 200 nm or less, which makes it possible to keep ozone dissolved in an aqueous solution over an extended time period of one month or more. Consequently, the effects obtainable from ozone can last with stability, so that sterilization and the like by use of ozone can be carried out in the field of medical care, the working site where food materials are handled, in the cultivation field of fish and shellfish and the livestock industry of land-dwelling creature, and so on. In addition, since ozone is retained in the form of nano-bubbles with bubble diameters of 200 nm or less, ozone can be taken in the body through the process of predation and breathing for fish and fishery, or through the process of drinking for land-dwelling creature. This makes it possible to wipe out harmful microorganism present in the body, such as bacteria, viruses and the like and inhibit the growth of the harmful microorganism.

INDUSTRIAL APPLICABILITY

According to the ozone water of the present invention and the production method therefor, ozone can be kept dissolved in the aqueous solution over an extended time period of one month or more. Consequently, the effects obtainable from ozone can last with stability, so that the present invention can be used in various fields where sterilization is needed, such as medical care, food-related industry, cultivation of fish and shellfish, the livestock industry of land-dwelling creature, and the like.

In addition, since ozone is retained in the form of nano-bubbles with bubble diameters of 200 nm or less, ozone can be taken in the body through the process of predation and breathing for fish and fishery or through the process of drinking for land-dwelling creature, which makes it possible to wipe out harmful microorganism present in the body, such as bacteria, viruses and the like and inhibit the growth of the harmful microorganism. The applicability is therefore expanded to the fields of medical care, cultivation of fish and shellfish and the like.

The invention claimed is:

1. An ozone water comprising an aqueous solution containing ozone nano-bubbles which hold ozone therein, the bubbles having a mean diameter of about 140 nm with a standard deviation of about 30 nm, with each of the ozone nano-bubbles surrounded by an inorganic shell consisting predominantly of electrolytic ions of iron, manganese, calcium, sodium, or magnesium, which inhibits the ozone nano-bubbles from dissipating.

2. A method for producing an ozone water, comprising the step of instantaneously shrinking ozone-containing microbubbles with diameter of 10 to 50 μm in an aqueous solution to generate ozone nano-bubbles having a mean diameter of about 140 nm with a standard deviation of about 30 nm by the application of a physical irritation to the ozone-containing microbubbles in the aqueous solution after the addition of electrolytic ions of iron, manganese, calcium, sodium, or magnesium, to the aqueous solution so that the electric conductivity of the aqueous solution reaches more than 300 μS/cm, wherein the ozone nano-bubbles with the mean diameter of about 140 nm, with a standard deviation of about 30 nm, are surrounded by an inorganic shell consisting predominantly of electrolytic ions of iron, manganese, calcium, sodium, or magnesium, which inhibits the ozone nano-bubbles from dissipating and are found to be stable in water after one week when the ozone water is placed in a glass bottle, and stored in a cool, dark place with the bottle being covered with a lid.

3. The method as claimed in claim 2, wherein the microbubbles are stopped from shrinking in such a manner that a charge density on the surface of each of the microbubbles is increased to evolve electrostatic repulsive forces when the diameter of the microbubbles is decreased in the step of instantaneously shrinking the microbubbles.

4. The method as claimed in claim 2, wherein the generated ozone nanobubbles are stabilized in such a manner that in the step of instantaneously shrinking the microbubbles, positively charged ones of the electrolytic ions are electrostatically attracted to ions of OH$^-$ adsorbed by a gas-liquid interface and drawn to a part adjacent to the gas-liquid interface in the aqueous solution, and accumulated in high concentrations within a minute volume, to form a shell surrounding each of the microbubbles so that the ozone in the microbubbles is inhibited from diffusing through the aqueous solution.

5. The method as claimed in claim 2, wherein the generated ozone nano-bubbles are stabilized in such a manner that adiabatic compression occurring in the step of instantaneously shrinking the microbubbles abruptly increases a temperature within each of the microbubbles to cause a physicochemical change involving an extremely high temperature around each of the microbubbles.

6. The method as claimed in claim 2, wherein the physical irritation is caused by electrically discharging the microbubbles using a discharger.

7. The method as claimed in claim 2, wherein the physical irritation is caused by irradiating the microbubbles with ultrasonic waves using an ultrasonic generator.

8. The method as claimed in claim 2, wherein the physical irritation is caused by compression, expansion and vortexes which occur when a flow is created in the aqueous solution by actuating a rotor set in a vessel holding the aqueous solution therein.

9. The method as claimed in claim 2, wherein the physical irritation is caused by compression, expansion and vortexes, in the case where a circulating circuit is provided in a vessel, in such a manner that the aqueous solution containing the microbubbles is introduced into the circulating circuit and then caused to pass through an orifice having a single opening or a plurality of openings or a porous plate which is provided in the circulating circuit.

* * * * *